United States Patent [19]

Toyama

[11] Patent Number: Plant 7,034

[45] Date of Patent: Sep. 19, 1989

[54] APRICOT TREE PA 7005-8

[75] Inventor: Thomas K. Toyama, Prosser, Wash.

[73] Assignee: Washington State University Research Foundation, Pullman, Wash.

[21] Appl. No.: 222,575

[22] Filed: Jul. 21, 1988

[51] Int. Cl.[4] ..... A01H 5/00

[52] U.S. Cl. ..... Plt./39

[58] Field of Search ..... Plt./39

*Primary Examiner*—Robert E. Bagwill

*Attorney, Agent, or Firm*—Chernoff, Vilhauer, McClung & Stenzel

[57] ABSTRACT

A new variety of apricot tree vigorously grows to a large size and bears large oval-shaped attractive fruits which are firm and early maturing. In addition, the fruits have long storage and shelf life thereby making them particularly adapted to early, premium, long-distance, fresh markets.

2 Drawing Sheets

BACKGROUND AND SUMMARY OF THE INVENTION

The present invention relates to a new and distinct variety of apricot tree which bears early maturing, uniformly large-sized frestone fruits of good quality and flavor and exceptional fimness which makes them well-suited for fresh market use. The fruits have long storage and shelf life and thus are suitable for shipping to premium, long-distance, fresh markets.

This new variety of apricot tree was originated at the Irrigated Agriculture Research and Extension Center at Prosser, Wash., from crosses made in 1970. It was selected in 1974 from among 166 seedlings of a cross between Rival (unpatented) and an unnamed plant designated P63-265 which was obtained as an open-pollinated seedling of Goldrich (unpatented). Second-test trees were planted on the Roza unit of the Center in 1976 and came into production in 1980.

The fruit of this variety ripens about 2½ weeks before Wenatchee (unpatented) in the Yakima Valley of Washington. Its large, oval-shaped fruit is 2¼ inches in diameter when adequately thinned. The skin is light-orange color with a trace of blush on exposed cheeks. The flesh is light-orange in color, firm, and moderately juicy. Some acidity is associated with the skin. Quality of the fruit is very good for fresh market use; however, canning quality is poor. The fruit has long storage and shelf life, which along with its firmness and large size makes it very attractive for shipping to early, premium, long-distance, fresh markets.

Trees of this variety are vigorous on apricot seedling rootstocks. They have not been tested on peach seedling rootstocks. The trees are large, vigorous and medium dense in growth habit. The flowers of the subject variety are partially self-fertile and may not require cross-pollination under some growing conditions.

Asexual reproduction of this new and distinct variety shows that its unique characteristics come true to form and are established and transmitted through succeeding propgations by grafting.

BRIEF DESCRIPTION OF THE DRAWINGS

In the accompanying photographs, vegetative growth and fruit of the new variety are shown both on and off the tree and are depicted in color as nearly true as is reasonably possible to make in color illustrations of this character.

DETAILED DESCRIPTION OF THE DISCLOSURE

Figure 1:
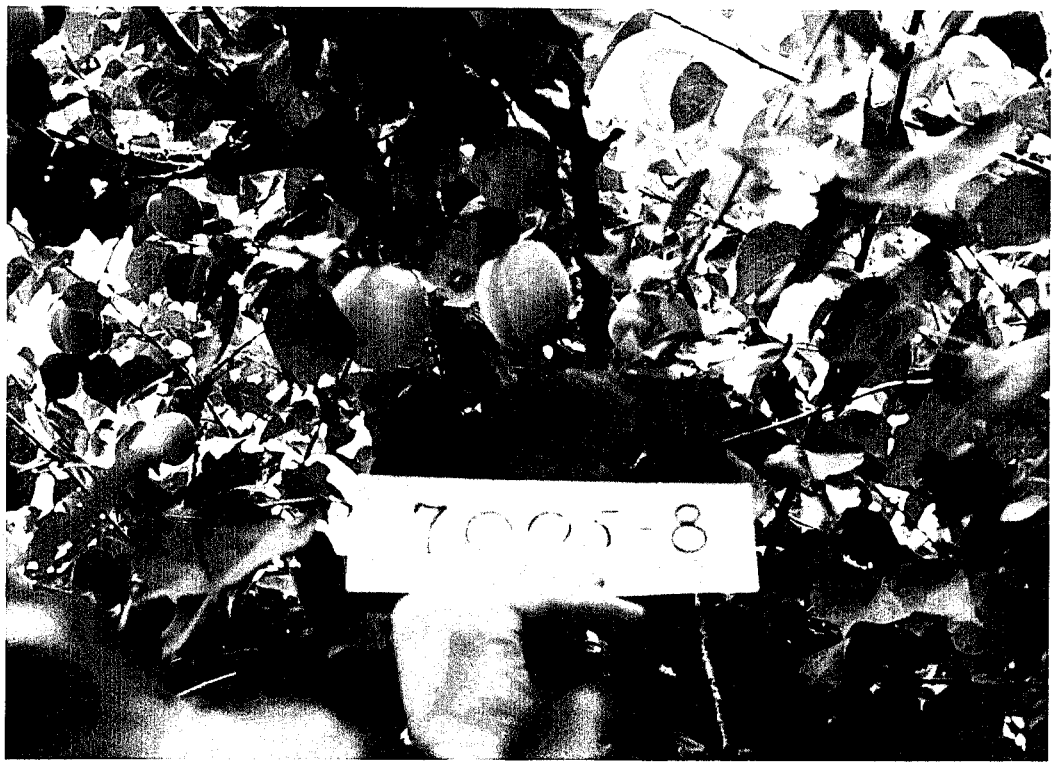
FIG. 1 shows the vegetative growth and fruit of a mature specimen of the subject variety on the tree.
Figure 2:
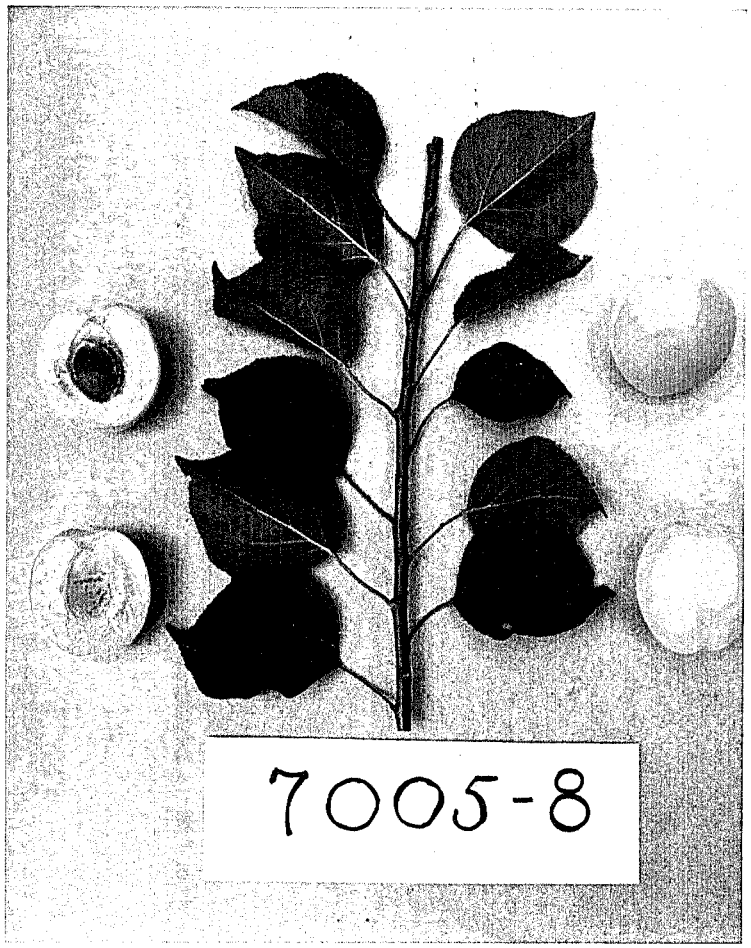
FIG. 2 shows the stems and leaves along with whole and half fruits of the subject variety off of the tree.

The following description was based on observations made of three second generation trees ranging in age from 4 to 11 years growing at the Irrigated Agriculture Research and Extension Center near Prosser, Wash., and of two five-year old second generation trees growing in a variety test plot at Parker, Wash. Color designations are to the Munsell Color Cascade Chart except where general color terms of ordinary dictionary significance are used.

Tree:
- *Size.*—Large.
- *Growth.*—Spreading.
- *Production.*—Very productive when adequately cross-pollinized.
- *Vigor.*—Very vigorous when placed on apricot seedling rootstocks.
- *Density.*—Dense.
- *Bearing.*—Regular.

Trunk:
- *Size.*—Thick, stocky.
- *Texture.*—Medium.

Branches:
- *Size.*—Medium stocky.
- *Texture.*—Smooth.
- *Lenticels.*—Large, numerous.
- *Color.*—Dark brown (29-16) to reddish brown (30-14).

Leaves:
- *Size.*—Large, average length 3⅜ inches to 4 inches, average width 3 inches to 3¾ inches.
- *Shape.*—Ovate, pointed.
- *Petiole.*—Average length, average thickness.
- *Glands.*—Usually two on blade and three to five on petiole, medium size, alternate, globose, greenish.
- *Margin.*—Finely serrate.

*Color.*—Upper surface — green (20-14), lower surface — light green (20-10).

Flower buds:

*Size.*—Medium.

*Shape.*—Conical.

*Length.*—Medium.

*Surface.*—Lightly pubescent.

Flowers:

*Date of bloom.*—Full bloom March 24.

*Size.*—Large.

*Color.*—Light pink to almost white when open, reddish sepals.

*Pubescence.*—Slight.

*Number of pistils.*—One.

*Number of stamens.*—Average 25–30.

Fruit:

*Maturity.*—Approximately 17 days before the variety Wenatchee, on or about July 7 at Prosser and Parker, Wash.

*Size.*—Uniformly large; diameter — $2\frac{1}{4}$ inches to $2\frac{3}{8}$ inches; transverse in suture plane, $2\frac{1}{8}$ inches to $2\frac{3}{8}$ inches; transverse at right angles to suture plane — $2\frac{1}{8}$ inches to $2\frac{3}{8}$ inches.

*Form.*—Uniform, oval, lateral compression lacking.

*Suture.*—Extends from base to apex, moderately distinct.

*Cavity.*—Rounded in suture plane, moderately shallow — $\frac{3}{8}$ inch, average breadth — $\frac{1}{2}$ inch.

*Base.*—Rounded to very slightly retuse, smoothly rounded on dorsal side, slightly rounded on suture side.

*Apex.*—Rounded.

*Pistil point.*—Slightly depressed.

*Stem.*—Length — $\frac{1}{4}$ inch, caliper — $\frac{1}{8}$ inch.

*Skin.*—Medium thickness, smooth, glossy, medium texture. Tendency to Crack: None. Down: Short, scant. Color: Orange ground (32-9), reddish blush (43-8) on portion of fruit exposed to sun. Tenacity: Tenacious to flesh.

*Flesh.*—Uniformity: Uniform ripening, slightly earlier at apex. Texture: Firm, fine-grained, meaty. Surface of Pit Cavity: Smooth. Juice: Moderately juicy. Flavor: Sweet, good flavor distinction, sub-acid. Aroma: Aromatic, pleasing. Color: Apricot (30-7). Eating Quality: Very good, distinct taste.

*Stone.*—Type: Freestone. Size: Medium large, average length — $1\frac{1}{8}$ inches, average breadth — 1-1/16 inches, average thickness — $\frac{5}{8}$ inch. Form: Ovate, rounded at base and slightly pointed at apex. Sides: Slightly pitted. Dorsal suture: Full with slight groove. Color: Light brown (28-13) to brown (28-15). Tendency to split: None.

Use: Fresh, local and long-distance markets.

Keeping Quality: Very good.

Shipping Quality: Very good.

What is claimed is:

1. A new and distinct variety of apricot tree obtained as a seedling from a seed parent entitled Rival (unpatented) and an unnamed pollen parent designated P63-265 which was obtained as an open-pollinated seedling of a variety entitled Goldrich (unpatented), is characterized by its large size and vigorous growth as well as its large, firm, attractive and flavorful fruits which mature early and have long storage and shelf life making them well-suited for shipment to early, long-distance, fresh markets, substantially as shown and described.

* * * * *